(12) United States Patent
Boezaart et al.

(10) Patent No.: US 9,724,070 B2
(45) Date of Patent: Aug. 8, 2017

(54) APPARATUS FOR FACILITATING ULTRASOUND-ASSISTED NEEDLE PLACEMENT FOR DRUG DELIVERY

(75) Inventors: Andre P. Boezaart, Gainesville, FL (US); Barys Ihnatsenka, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 687 days.

(21) Appl. No.: 14/236,695

(22) PCT Filed: Jul. 31, 2012

(86) PCT No.: PCT/US2012/049023
§ 371 (c)(1),
(2), (4) Date: Feb. 3, 2014

(87) PCT Pub. No.: WO2013/019806
PCT Pub. Date: Feb. 7, 2013

(65) Prior Publication Data
US 2014/0200445 A1   Jul. 17, 2014

Related U.S. Application Data

(60) Provisional application No. 61/513,791, filed on Aug. 1, 2011.

(51) Int. Cl.
*A61B 5/05* (2006.01)
*A61B 8/08* (2006.01)
*A61M 5/158* (2006.01)
*A61B 8/00* (2006.01)
(Continued)

(52) U.S. Cl.
CPC .......... *A61B 8/0841* (2013.01); *A61B 8/4209* (2013.01); *A61B 8/4455* (2013.01); *A61M 5/158* (2013.01); *A61M 25/065* (2013.01); *A61M 25/09* (2013.01); *A61B 2562/16* (2013.01)

(58) Field of Classification Search
None
See application file for complete search history.

(56) References Cited

U.S. PATENT DOCUMENTS

| 5,427,108 A | 6/1995 | Bollinger |
| 5,988,824 A * | 11/1999 | Rowsey, Jr. ......... A61B 17/062 128/898 |
| 6,379,307 B1 | 4/2002 | Filly |

(Continued)

FOREIGN PATENT DOCUMENTS

WO   2008024515   2/2008

OTHER PUBLICATIONS

International Search Report and Written Opinion Dated Mar. 4, 2013.

*Primary Examiner* — Jonathan Cwern
*Assistant Examiner* — Amelie R Gillman
(74) *Attorney, Agent, or Firm* — Thomas Horstemeyer LLP

(57) ABSTRACT

In one embodiment, apparatus for facilitating ultrasound-assisted needle placement for drug delivery includes an ultrasound probe cover adapted to receive an ultrasound probe, the cover comprising a first wall and a needle guide associated with the first wall, the needle guide comprising an element adapted to guide a needle into a patient adjacent the cover.

14 Claims, 11 Drawing Sheets

(51) Int. Cl.
*A61M 25/06* (2006.01)
*A61M 25/09* (2006.01)

(56) References Cited

U.S. PATENT DOCUMENTS

| | | | |
|---|---|---|---|
| 6,485,426 B2 * | 11/2002 | Sandhu | A61B 8/0833 600/461 |
| 6,695,786 B2 * | 2/2004 | Wang | A61B 8/0833 600/417 |
| 2004/0049134 A1 * | 3/2004 | Tosaya | A61H 23/0236 601/2 |
| 2005/0096547 A1 * | 5/2005 | Wendelken | A61B 8/4209 600/459 |
| 2006/0064010 A1 * | 3/2006 | Cannon | A61B 17/3403 600/434 |
| 2006/0105288 A1 * | 5/2006 | Garfinkel | A61B 1/247 433/31 |
| 2007/0016135 A1 * | 1/2007 | Kanner | A61M 5/46 604/117 |
| 2007/0073155 A1 * | 3/2007 | Park | A61B 8/0833 600/461 |
| 2009/0143684 A1 * | 6/2009 | Cermak | A61B 8/0841 600/461 |
| 2010/0041990 A1 | 2/2010 | Schlitt | |
| 2010/0160787 A1 * | 6/2010 | Gorzitze | A61B 8/0833 600/461 |
| 2010/0312121 A1 | 12/2010 | Guan | |
| 2012/0259219 A1 * | 10/2012 | Sheldon | A61B 17/3403 600/439 |

* cited by examiner

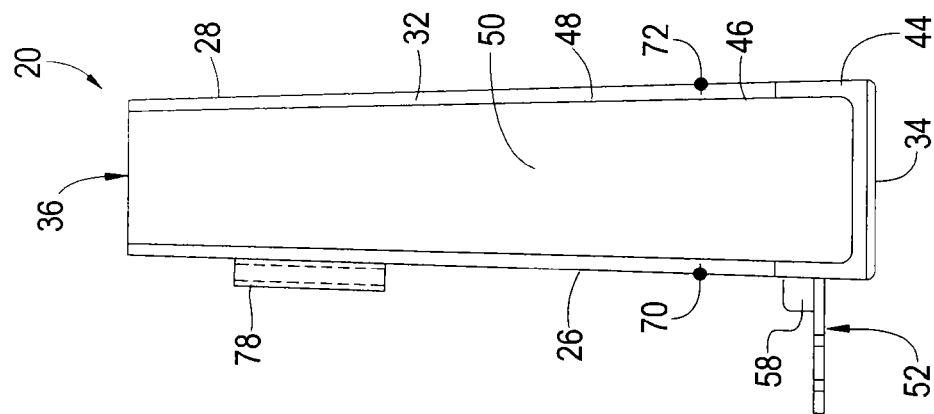
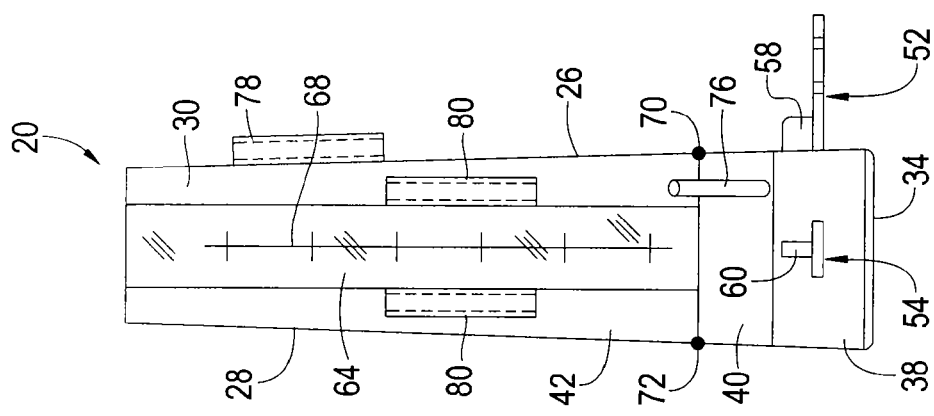
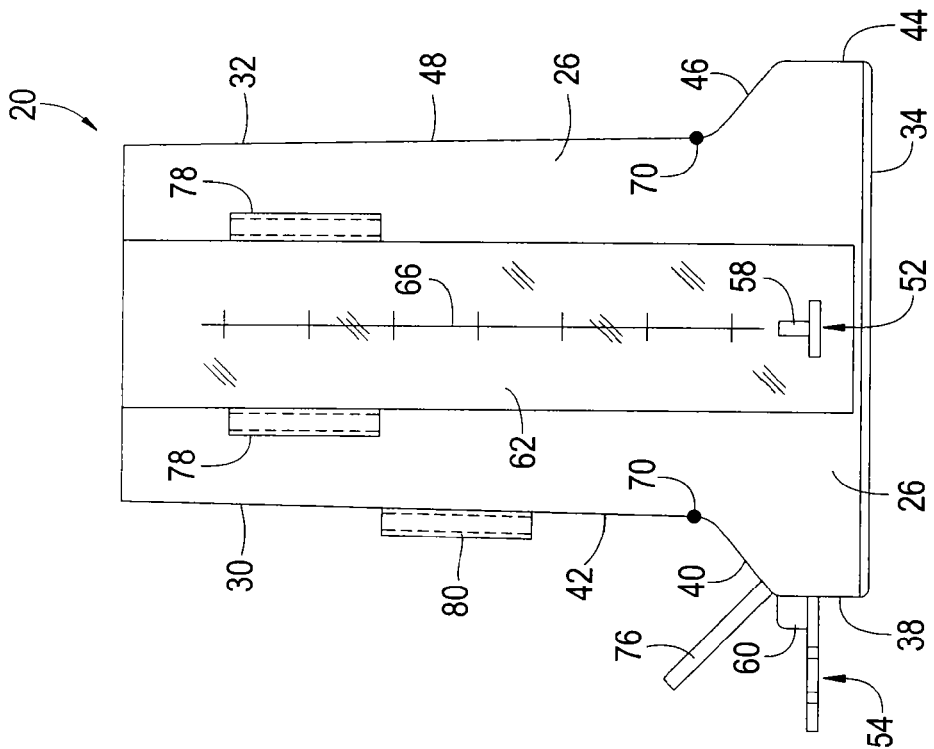

APPARATUS FOR FACILITATING ULTRASOUND-ASSISTED NEEDLE PLACEMENT FOR DRUG DELIVERY

CROSS-REFERENCE TO RELATED APPLICATION(S)

This application is the 35 U.S.C. §371 national stage of PCT application PCT/US2012/049023, filed Jul. 31, 2012, which claims priority to and the benefit of U.S. Provisional Application Ser. No. 61/513,791, filed Aug. 1, 2011, both of which are hereby incorporated by reference herein in their entirety.

BACKGROUND

Ultrasound imaging is widely used to assist with needle placement in medical procedures in which a drug is to be delivered to a target region within the body, such as the case with peripheral nerve blocks. In such a procedure, ultrasound imaging is used to identify the target region and to visualize the needle to assist the physician in guiding the tip of the needle to the target region.

There are various drawbacks associated with current ultrasound-assisted drug delivery procedures. One such drawback relates to the positioning and holding of the drug delivery needle. Physicians typically use a freehand placement technique for positioning the needle using ultrasound guidance. In such a technique, the non-dominant hand (e.g., the left hand) is used to hold the ultrasound probe against the patient's skin and the dominant hand (e.g., the right hand) is used to guide the needle tip to the target region with reference to image data collected by the probe. The needle must be carefully manipulated by the physician using a dynamic process in order to position the tip within the target region. Once the needle tip has been placed in the correct position, the physician must hold the needle steady. When a single injection is to be administered, a further physician or a physician's assistant must depress a plunger to deliver the drug to the target region. When the drug is to be continuously delivered, the further physician or physician's assistant must pass a catheter through the needle so that the tip of the catheter is also placed in the target region. Such procedures are undesirable because multiple persons are needed to perform it correctly.

Another drawback of current ultrasound-assisted drug delivery procedures is that the ultrasound probe typically must be used with a sheath to maintain the sterility of the operating environment, and such sheaths are often both costly and cumbersome. In addition, the index matching gel that is used to ensure that ultrasonic waves can pass from the sheathed probe and into the patient is messy and can foul the operating environment.

As can be appreciated from the above description, it would be desirable to have apparatus that enables the physician to avoid one or more of the above-described drawbacks associated with current ultrasound-assisted drug delivery procedures.

BRIEF DESCRIPTION OF THE DRAWINGS

The present disclosure may be better understood with reference to the following figures. Matching reference numerals designate corresponding parts throughout the figures, which are not necessarily drawn to scale.

FIG. 3 is a front view of the ultrasound probe cover of FIG. 2.

FIG. 4 is a first side view of the ultrasound probe cover of FIG. 2.

FIG. 5 is a second side view of the ultrasound probe cover of FIG. 2.

DETAILED DESCRIPTION

As described above, it would be desirable to have apparatus that enables a physician to avoid one or more of the drawbacks associated with current ultrasound-assisted drug delivery procedures. Described herein is apparatus that provides an all-in-one solution that overcomes many of those drawbacks. In some embodiments, the apparatus comprises a sterile cover in which the ultrasound probe can be placed. Provided on the cover is one or more needle guides that can be used to position a needle both before and after its insertion into the body. In some embodiments, the cover further comprises alignment means that assist the physician in aligning the needle relative to the probe. In still other embodiments, the cover also comprises a base that contains a sterilization fluid within a space between the cover and the patient's skin to both sterilize the skin and provide for index matching between the probe and the patient. In yet other embodiments, the cover additionally comprises or can be used in conjunction with means for supporting and holding the needle in a desired position relative to the probe to free up the physician's hand when a catheter is to be placed within the patient.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
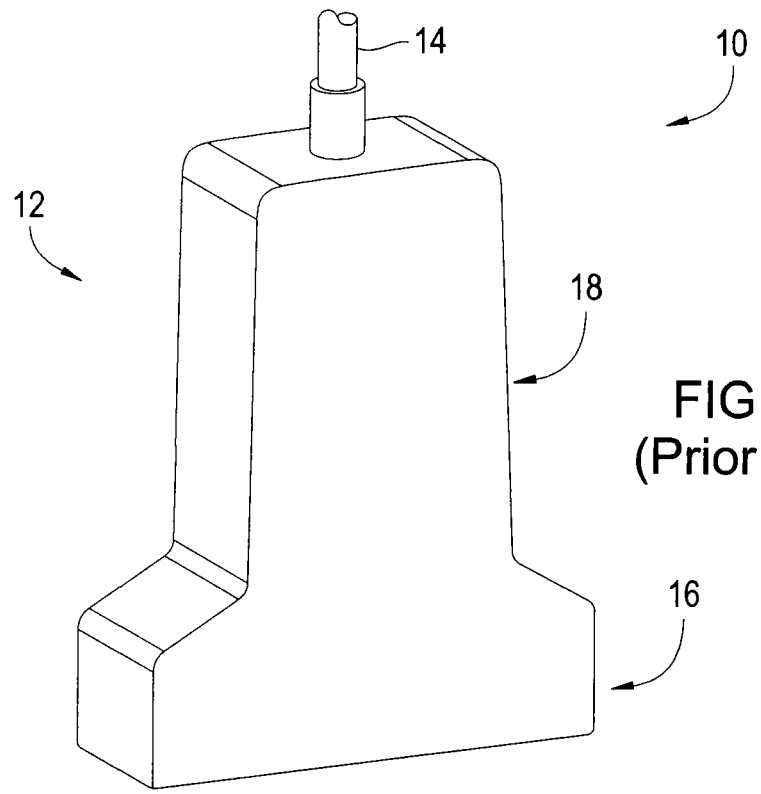
FIG. 1 is a perspective view of a conventional ultrasound probe.

FIG. 1 illustrates an example conventional ultrasound probe 10 of the type that may be used in an ultrasound-assisted drug delivery procedure, as when a peripheral nerve block is to be performed. As is apparent from FIG. 1, the probe 10 generally comprises a body 12 and a cord 14 that extends from the body. As is also shown in FIG. 1, the body 12 comprises a relatively wide lower portion 16 and a relatively narrow upper portion 18. The lower portion 16 of the body 12 forms the head of the ultrasound probe 10, which can be applied to the skin of a patient to deliver ultrasonic waves into the patient's body for purposes of ultrasonic imaging of the structures therein.

FIGS. 2-6 illustrate an embodiment of an ultrasound probe cover 20 that can be used with an ultrasound probe, such as the ultrasound probe 10 of FIG. 1. In some embodiments, the cover 20 is unitarily formed from of a single piece of polymeric material. In such a case, the polymeric material can be clear to enable one to see the probe 10 through the cover 20. As is apparent from FIG. 2, the cover 20 can have a shape and size that is similar to those of the probe 10. This enables the cover 20 to snuggly fit onto the probe 10 with little space between the cover and the probe. As is described below, index-matching gel can be placed along the bottom of the inside of the cover 20 to ensure that there are no air gaps between the probe head and the cover.

Figure 2:
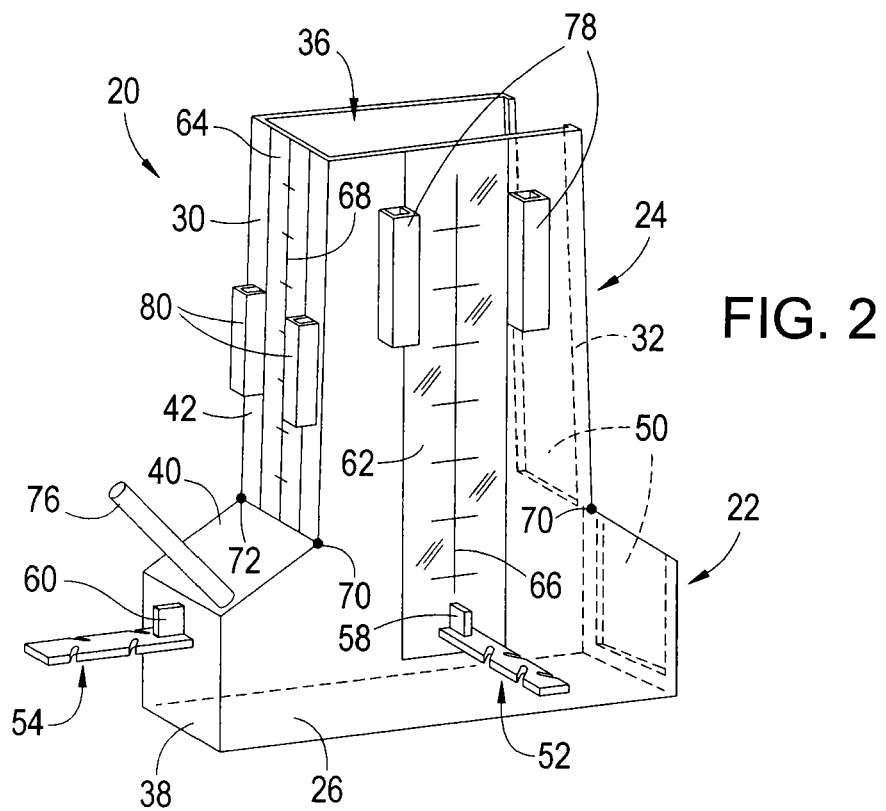
FIG. 2 is a front perspective view of an embodiment of an ultrasound probe cover that can be placed around an ultrasound probe, such as the probe of FIG. 1.

Although the particular configuration of the cover 20 is dictated at least in part by the configuration of the ultrasound probe with which is to be used, the cover shown in FIG. 2 generally includes a relatively wide first or lower portion 22 and a relatively narrow second or upper portion 24 that extends outward (upward) from the lower portion. The cover 20 can be said to generally comprise a front side, a rear side, first and second lateral sides, a bottom side, and a top side. The front side is defined by a front wall 26, the rear side is defined by a rear wall 28 (see FIGS. 5 and 6), the first and second lateral sides are defined by a first lateral (left) wall 30 and a second lateral (right) wall 32, the bottom side is defined by a footplate 34 (FIG. 6), and the top side is defined by an opening 36.

In some embodiments, the front wall 26 and the rear wall 28 can be generally planar, while the lateral walls 30, 32 can comprise multiple planar sections that are angled relative to each other. In the example of FIG. 2, the left wall 30 comprises a first or bottom section 38, a second or middle section 40, and a third or top section 42. In similar manner, the right wall 32 comprises a first or bottom section 44, a second or middle section 46, and a third or top section 48. Of course, in other embodiments, the lateral walls 30, 32 can also be planar, and/or the front and rear walls 26, 28 can be comprise multiple sections. As with the cover 20 in general, the configuration of the walls of the cover is dictated at least in part by the configuration of the ultrasound probe with which the cover is to be used.

As is shown best in FIGS. 2 and 5, the right wall 32 comprises an elongated opening 50 that joins the opening 36 provided at the top side of the cover 20. The openings 36, 50 together form a gap through which the ultrasound probe can be passed to place the probe within the cover 20. In embodiments in which the cover 20 is made of a flexible material, such as flexible polymeric material, the cover can deform to enable passage of the probe into an interior space of cover, and the cover can then snap back into its original shape so as to closely conform to the contours of the probe. In such cases, the cover 20 can be said connect to the probe in a snap-fit manner.

Figure 7:
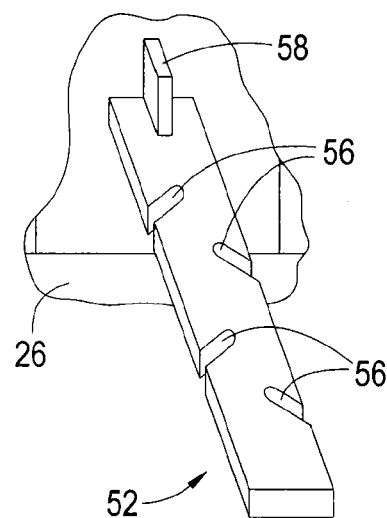
FIG. 7 is a detail view of a needle guide of the ultrasound probe cover of FIG. 2.

As noted above, the cover 20 can include one or more needle guides that assist the physician with positioning a needle relative to the ultrasound probe. In the embodiment of FIG. 2, the cover 20 includes two such needle guides, a first or front needle guide 52 and a second or lateral needle guide 54. As is further illustrated in FIG. 2, the front needle guide 52 extends out from the front wall 26 in the lower portion 22 of the cover 20 in a direction that is generally perpendicular to the front wall, and the lateral needle guide 54 extends out from the bottom section 38 of the left wall 30 in the lower portion of the cover in a direction that is generally perpendicular to the bottom section. FIG. 7 shows the front needle guide 52 in detail. Notably, the lateral needle guide 54 can have a similar or identical configuration.

As is illustrated in FIG. 7, the needle guide 52 can comprise a rigid, elongated member that is provided with one or more elements that assist in guiding a needle. In the example of FIG. 7, the member has a rectangular cross-section and multiple needle slots 56 that extend inward from the lateral edges of the member along a diagonal direction toward the front wall 26. Each of the slots 56 has a width dimension that is slightly larger than the diameter of a needle that is to be used with the cover 20. The needle can therefore be inserted into a selected slot 56 and advanced along its length until reaching the end of the slot, which can be located a predetermined distance from the front wall 26. By way of example, the slots 56 can be arranged so that their ends are positioned approximately 2 millimeters (mm), 4 mm, 6 mm, and 8 mm away from the front wall 26. In some embodiments, such distances can be marked on the needle guides 52, 54. Regardless, the physician can easily position the needle in a particular desired distance from the front wall 26 of the cover 20 and, therefore, from the front side of the ultrasound probe. It is noted that the design of the needle guides 52, 54 can be altered and still provide the same functionality. For example, instead of slots 56 that extend inward from the lateral edges of the guides 52, 54, the slots could alternatively extend outward from an elongated inner slot that extends along the length of the guides. In addition, while the guide 52 is shown having four slots 56, it will be appreciated that fewer or greater slots or other guide means could be used.

As is further illustrated in FIG. 7, a vertically-aligned, planar tab 58, the purpose of which is described below, can extend upwardly from the needle guide 52 at or near the front wall 26. As is shown in FIG. 2, the needle guide 54 can comprise a similar vertically-aligned, planar tab 60.

With further reference to FIG. 2, the front and left walls 26 and 30 can be provided with alignment means that assist the physician in aligning the needle relative to the probe. In the illustrated embodiment, the alignment means include a first or front mirror 62 and a second or lateral mirror 64. The front mirror 62 is marked with a vertical line 66 and the lateral mirror 64 is marked with a vertical line 68. As is described below, the vertical lines 66 and 68 assist the physician in maintaining the alignment of the needle when using an out-of-plane approach and an in-plane approach, respectively. As is further shown in FIG. 2, depth markers can be provided along the lengths of the vertical lines 66, 68. As is also described below, the depth markers together form a scale that provides an indication of the depth to which the needle has been inserted into the patient.

The alignment means further comprise several markers that are provided on the cover 20 at discrete positions. In the illustrated embodiment, the markers include two front markers 70 and two rear markers 72. The front markers 70 are positioned along the edges of the cover 20 defined by the front wall 26 and the lateral walls 30 and 32. More specifically, one front marker 70 is positioned along the edge of the front wall 26 and the left wall 30 at the intersection of its middle section 40 and top section 42, and the other front marker 70 is positioned along the edge of the front wall and the right wall 32 at the intersection of its middle section 46 and top section 48. The rear markers 72 are positioned along the edges defined by the rear wall 28 and the lateral walls 30 and 32. More specifically, one rear marker 72 is positioned along the edge of the rear wall 28 and the left wall 30 at the intersection of its middle section 40 and top section 42, and the other rear marker 72 is positioned along the edge of the rear wall and the right wall 32 at the intersection of its middle section 46 and top section 48. As is described below, alignment of the needle can be performed using the mirrors 62, 64 in conjunction with the markers 70, 72.

Further provided on the cover 20 is a reference element 76 that provides the physician with an indication of a 45° approach angle when inserting a needle using an in-plane approach. Specifically, if the needle is parallel to the reference element 76, which forms a 45° angle with the base plate 34 of the cover 20, and therefore the skin surface, the needle is oriented at a 45° angle relative to the patient.

With further reference to FIG. 2, the cover 20 can also include mounting elements that are adapted to receive and secure mating mounting elements of support means that can be used to support a needle relative to the cover. In the illustrated embodiment, the mounting elements comprise front mounting elements 78 and lateral mounting elements 80. In some embodiments, the mounting elements 78, 80 can comprise vertically-aligned tubes that are positioned along the edges of the mirrors 62 and 64, respectively, that are adapted to receive vertically aligned tangs of the support means, as is described below. As is shown in FIG. 2, the tubes can have rectangular cross-sections.

Figure 6:
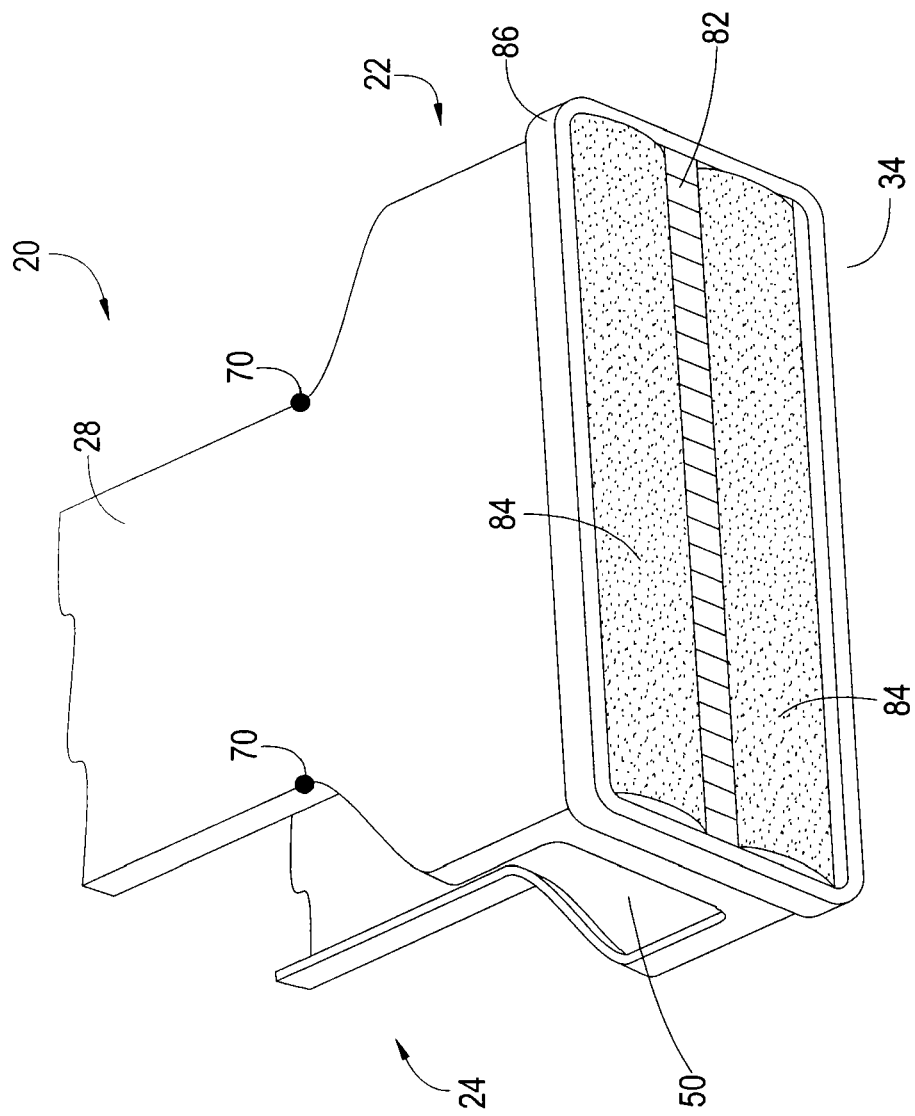
FIG. 6 is a bottom perspective view of the ultrasound probe cover of FIG. 2.

FIG. 6 illustrates the configuration of the base plate 34 of the cover 20. A is shown in that figure, the base plate 34 comprises an elongated window 82 through which the ultrasonic waves of the probe can pass. Positioned on both sides of the window 82 are absorbent elements 84 that are adapted to absorb and hold a sterilizing fluid, such as chlorhexidine. In some embodiments, the absorbent elements 84 comprise sponges. Surrounding the absorbent elements 84 and the window 82 is a peripheral skirt 86. In some embodiments, the skirt 86 is made of a resilient material, such as silicone or rubber, that enables the skirt to easily conform to the contours of the patient. When the cover 20 and its probe are gently pressed against the skin of the patient, the absorbent elements 84 are compressed and the sterilizing fluid they contain fill any gaps between the window 82 and the skin so as to form a pathway for the ultrasonic waves to travel. The skirt 86 prevents the sterilizing fluid from escaping the footprint of the cover 20. With such operation, the sterilizing fluid serves not only to sterilize the skin of the patient but also to provide index matching between the cover 20 and the patient's skin.

Having described the cover 20 and its various components, use of the cover will now be discussed. As mentioned above, an ultrasound probe, like the probe 10 shown in FIG. 1, can be inserted into the cover 20 by passing the probe through the gap created by the openings 36 and 50. Prior to placing the probe within the cover 20, however, index-matching gel can be placed at the bottom of the inside of the cover to ensure that no air gaps exist between the head of the probe and the inside of the cover, which could interfere with the transmission and reception of ultrasonic waves generated by the probe. Because the index-matching gel is contained within the cover 20, the procedure is much less messy and the gel will not foul the operating environment.

Figure 8:
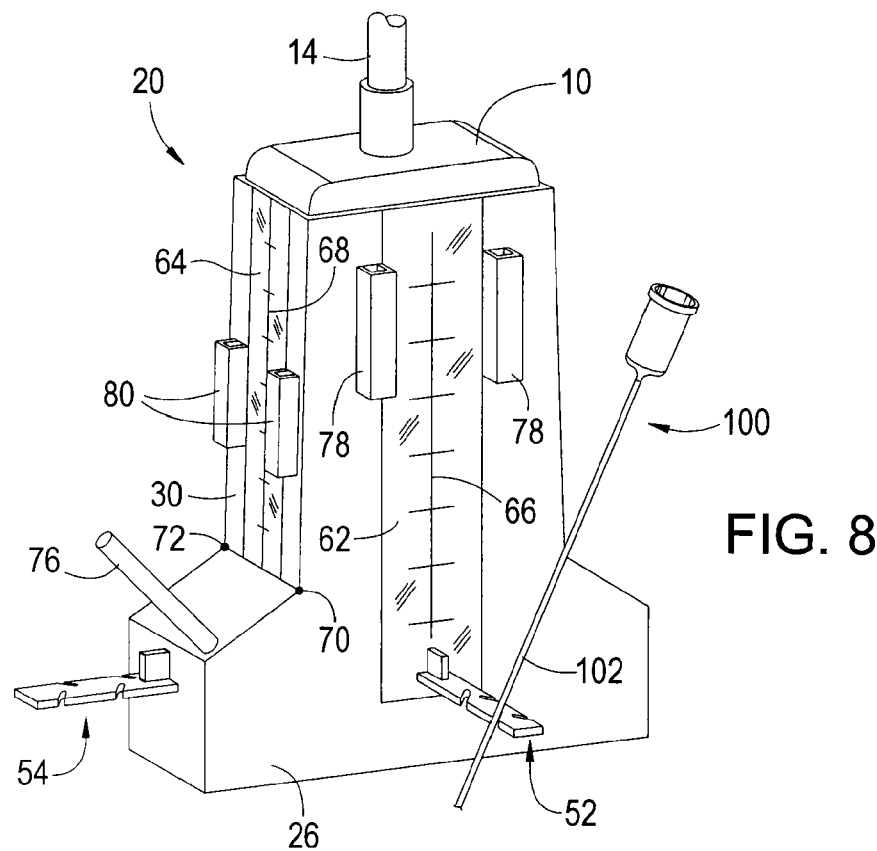
FIG. 8 is a front perspective view of the ultrasound probe cover of FIG. 2 applied to an ultrasound probe and a needle being inserted into patient using a needle guide of the cover.

FIG. 8 illustrates the ultrasound probe 10 inserted within the cover 20. As is apparent from that figure, the cover 20 fits snuggly around the probe 10 and is therefore not cumbersome or obstructive. When a drug is to be delivered to a target region within a patient, the covered probe 10 can be placed on the skin above the target region. As noted above, the absorbent elements 84 of the footplate 34 of the cover can be provided with a sterilizing fluid. Therefore, when the covered probe 10 is placed on the skin of the patient, that fluid bathes the window 82 to ensure that ultrasonic waves emanating from the covered probe can enter the patient's body, and that the reflected waves return to the probe. As was also noted above, the skirt 86 ensures that the fluid does not escape the space between the cover's footplate 34 and the skin surface.

The location of the target region can be identified by ultrasonic imaging using the probe 10. Once that region has been identified, a needle can be inserted into the patient so that a drug, such as an anesthetic, can be delivered to that region. FIG. 8 illustrates an example in which a needle 100 is to be inserted using an out-of-plane approach in which the needle is not within the plane of the ultrasonic waves emitted by the probe 10. In the example of FIG. 8, this means that the shaft 102 of the needle 100 is inserted from the front side of the cover 20. As is shown in FIG. 8, the insertion of the needle 100 can be guided using one of the slots 56 of the needle guide 52. As described above, the needle shaft 102 can be passed along the length of the slot 56 until it reaches the end of the slot.

Figure 9:
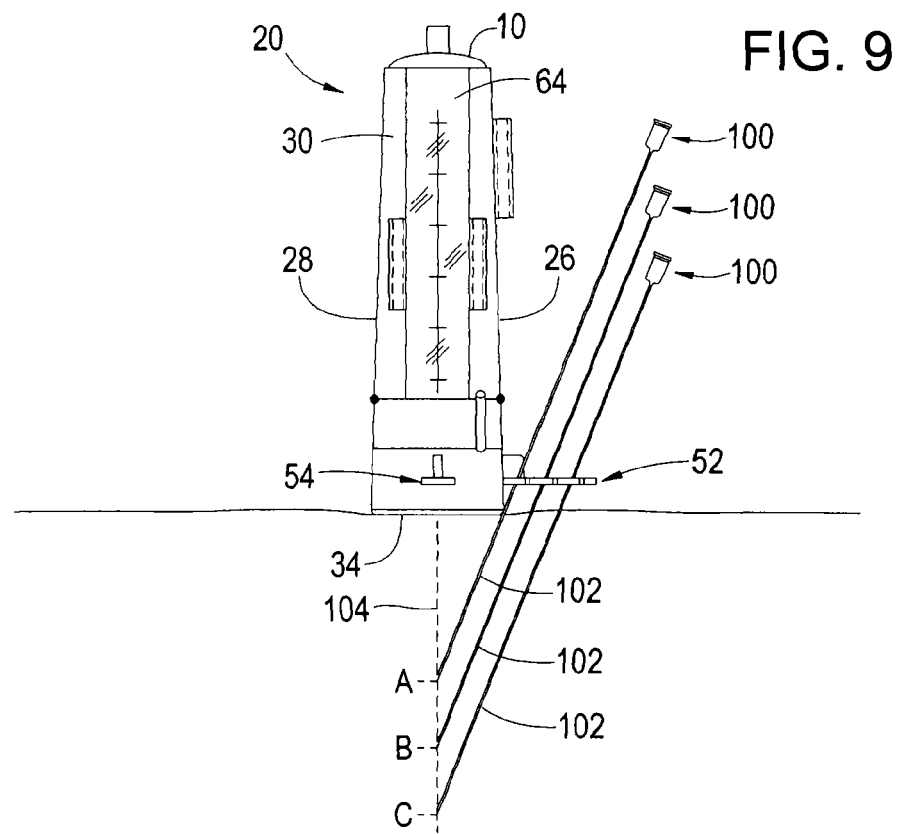
FIG. 9 is a side view of the ultrasound probe cover of FIG. 2, illustrating use of different guide slots of a needle guide of the cover.
Figure 10:
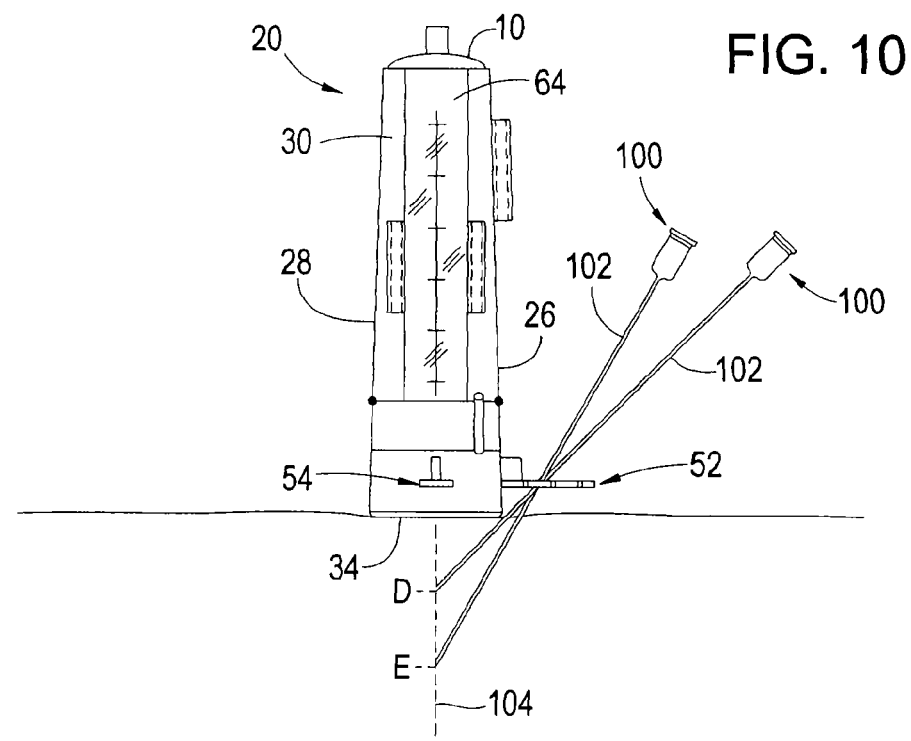
FIG. 10 is a side view of the ultrasound probe cover of FIG. 2, illustrating alternative angles that can be achieved with a guide slot of a needle guide of the cover.

Referring next to FIG. 9, illustrated are three different needles 100 that are guided by three different slots 56 of the front needle guide 52. As can be appreciated from that figure, the slot 56 that is selected has an effect on the depth at which the needle 100 crosses the plane 104 of the ultrasonic waves. In particular, the farther the slot 56 is from the front wall 26 of the cover 20, the deeper the point at which the tip of the needle 100 will intersect the plane 104, assuming the same angle of insertion. In FIG. 9, three different depths are reached at points A, B, and C, wherein point B is deeper than point A, and point C is deeper than point B. As is depicted in FIG. 10, the slots 56 of the needle guides 52, 54 are not so restrictive as to prevent the physician from manipulating the needle 100 while within a slot. In particular, the physician is free to adjust the angle of insertion while the needle shaft 102 is within a given slot 56. Therefore, the needle 100 can be inserted with a relatively shallow angle to reach a relatively shallow depth D, or can be inserted with a relatively large angle to reach a relatively deep depth E.

Figure 11:
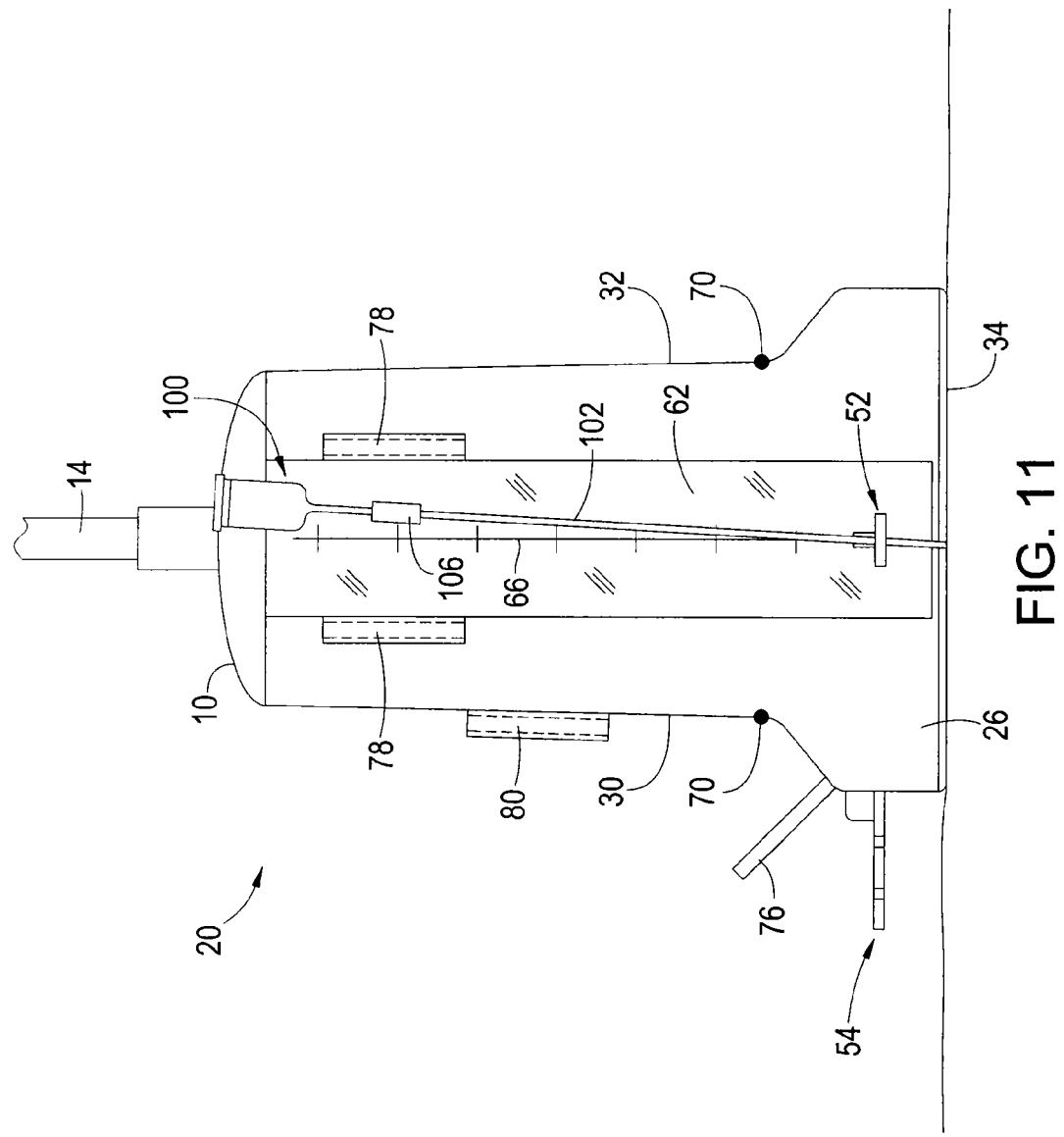
FIG. 11 is a front view of the ultrasound probe cover of FIG. 2 applied to an ultrasound probe, illustrating insertion of a needle with the assistance of alignment means of the cover.

The alignment means can be used to ensure that the needle 100 is straight relative to the cover 20 and the probe 10 before it is inserted into the patient. As is shown in FIG. 11, the needle shaft 102 can be aligned with the vertical line 66 provided on the mirror 62 on the front wall 26 of the cover 20. More particularly, the physician can confirm that the needle shaft 102 reflected in the mirror 62 aligns with the vertical line 66. This ensures that the needle shaft 102 is not misaligned with the probe 10, as is the case depicted in FIG. 11. Because the physician could mistakenly believe that the needle shaft 102 is aligned with the vertical line 66 when the physician is not aligned with the mirror 62 because of parallax error, the physician can use the most distant markers, in this case the rear markers 72, to ensure that he or she is looking at the mirror head-on. When the physician can see both of the most distant markers at the same time, this means that they are not obscured by the walls of the cover 20, as when the physician's perspective is not centered relative to the cover. In such a case, the physician knows that he or she is correctly aligned with the mirror 62 and that, if the needle shaft 102 appears to be aligned with the vertical line 66, the needle 100 is properly aligned relative to the probe. The mirror 64 and its vertical line 68 can be used in similar manner for in-plane approaches from the left side of the cover 20.

Figure 12A:
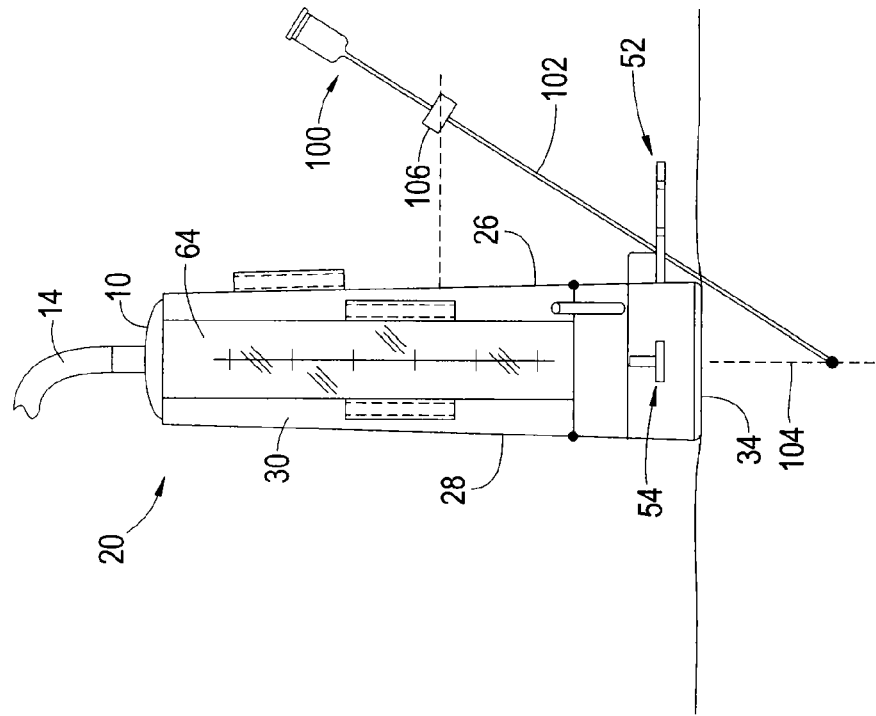
FIGS. 12A and 12B are side views of the ultrasound probe cover of FIG. 2 applied to an ultrasound probe, illustrating insertion of a needle with the assistance of a gauge provided on the cover.
Figure 12B:
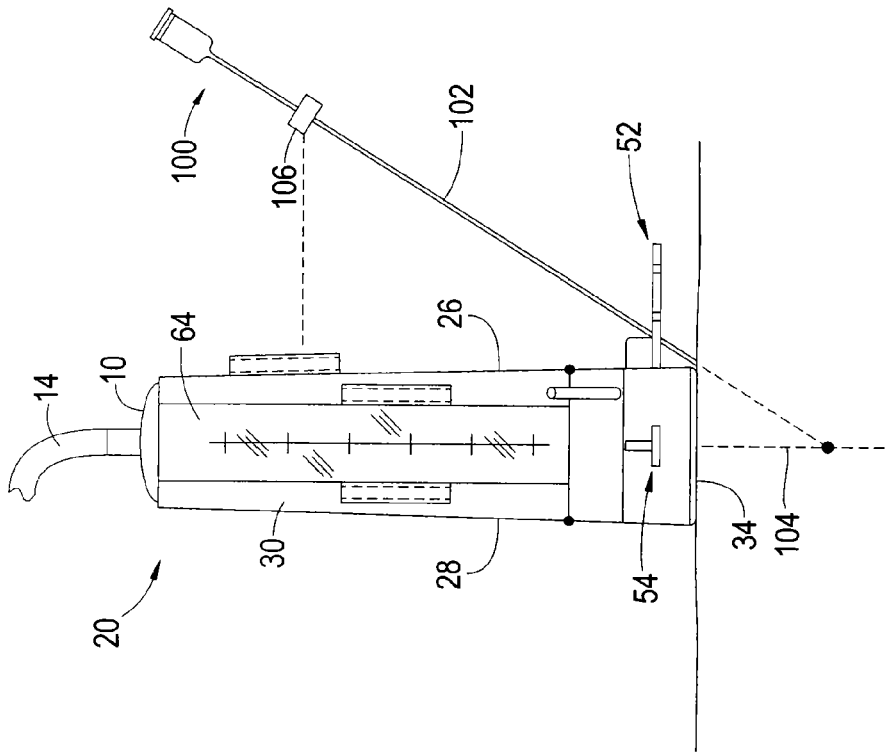

Referring next to FIGS. 12A and 12B, the mirror 62 and its scale defined by its vertical line 66 and its depth markers can be used by the physician to obtain a general indication of the depth of the needle tip. As is shown in those figures, the needle 100 can be provided with a marker 106 that can be viewed in the mirror 62 and compared with the scale. At an initial state before the needle 100 has been inserted (FIG. 12A), the marker 106 will align with a first position on the scale of the mirror 62. After the needle 100 has been inserted (FIG. 12B), the depth of insertion can be estimated by viewing the new position of the marker 106 relative to the scale of the mirror 62. The mirror 64 and its scale can be used in similar manner for in-plane approaches from the left side of the cover 20.

Figure 13:
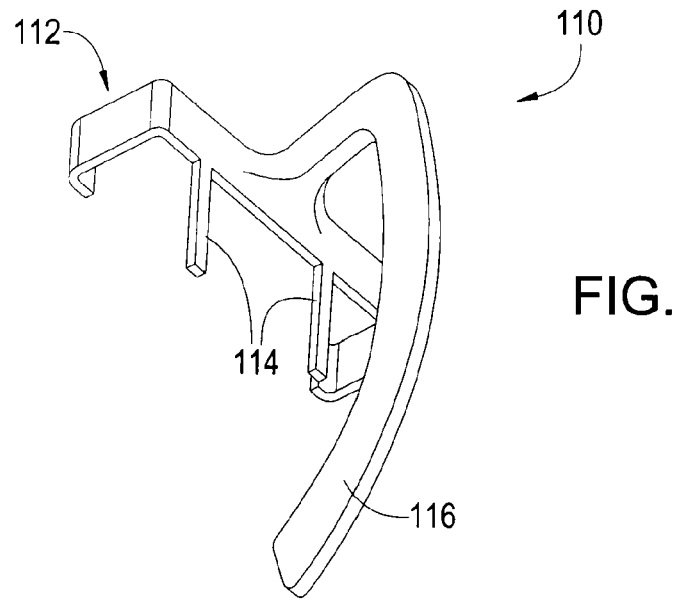
FIG. 13 is a perspective view of a needle support that can be used in conjunction with the ultrasound probe cover of FIG. 2.
Figure 14:
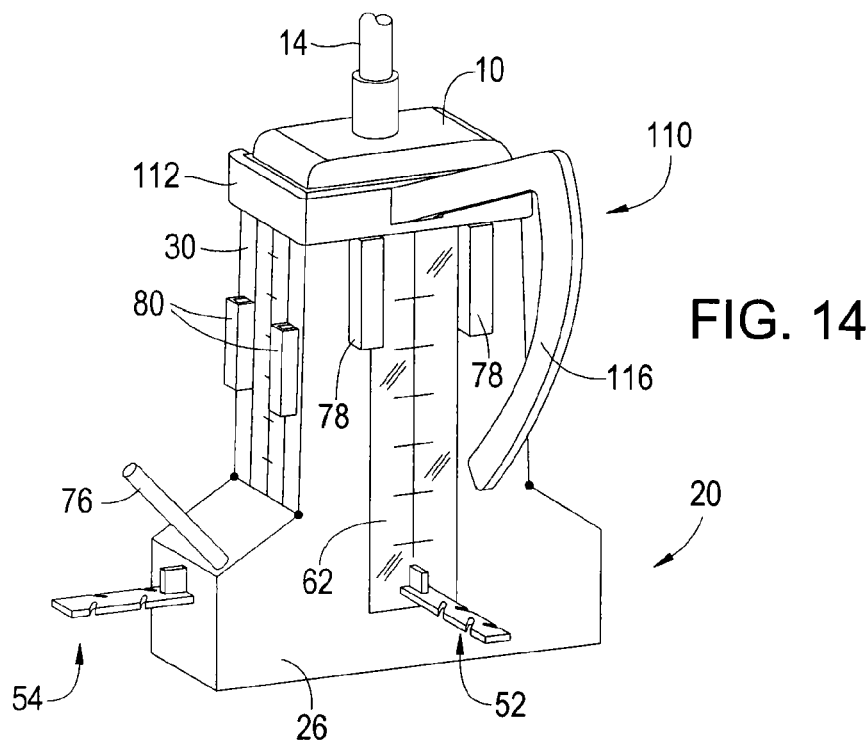
FIG. 14 is a front perspective view of the ultrasound probe cover of FIG. 2 with the needle support of FIG. 13 attached to the cover.

In cases in which a catheter is to be inserted into the patient for continuous delivery of a drug, needle support and holding means can be used to secure a needle relative to the cover 20 and the probe 10 to free up the physician's hand to insert the catheter, or a guidewire that will be used to guide the catheter, through the needle to the target site. FIG. 13 illustrates a needle support 110 that can be used with the cover 20 to support a needle. As is shown in FIG. 13, the needle support 110 comprises a clip portion 112 that is adapted to wrap around the cover 20, vertically-aligned tangs 114 that extend downward from the clip portion that are adapted to slide within the mounting elements 78 of the cover, and a curved arm 116 that extends outward and downward from the clip portion to which a needle can be connected. FIG. 14 illustrates the needle support 110 mounted to the cover 20. In FIG. 14, the clip portion 112 of the needle support 110 is wrapped around the top edge of the cover 20 and the tangs 114 are received within the mounting elements 78. As is also shown in FIG. 14, the arm 116 is positioned in front of the front side of the cover 20. In that position, a needle can be attached to the arm 116 when an out-of-plane approach is used.

Figure 16:
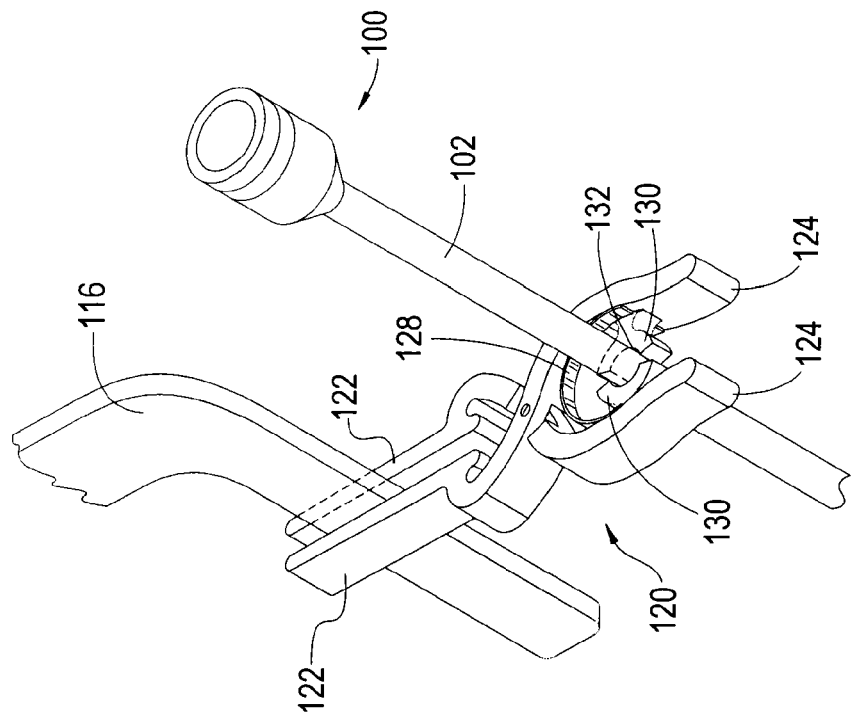
FIG. 16 is a top perspective view of the needle holder of FIG. 15 as attached to the needle support of FIG. 13.
Figure 15:
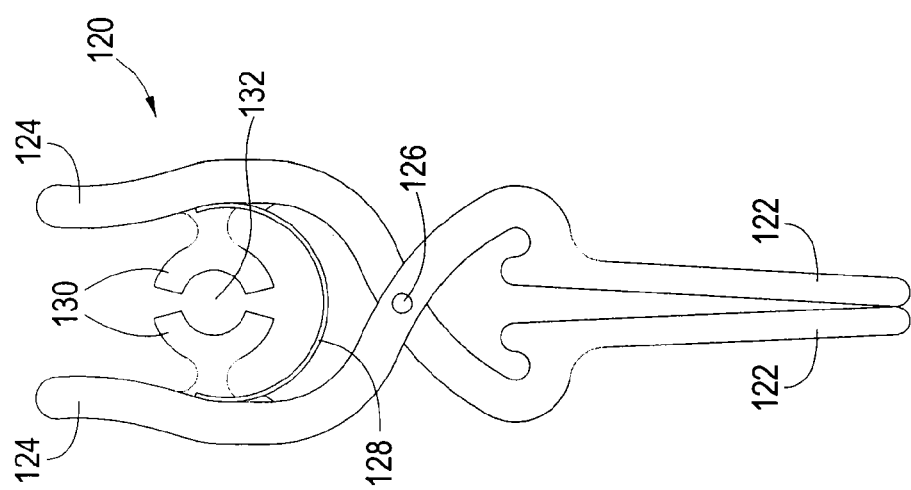
FIG. 15 is a top view of a needle holder that can be used in conjunction with the needle support of FIG. 13.

FIGS. 15 and 16 illustrate a needle holder 120 that can be used to secure a needle to the arm 116 of the needle support 110. With reference first to FIG. 15, the needle holder 120 takes the form of a biased clip having opposed clamping jaws 122 and opposed finger tabs 124. In the illustrated embodiment, the needle holder 120 comprises two separate members, each comprising a clamping jaw 122 and a finger tab 124, that are pivotally connected to each other with a pin 126. A biasing element 128 in the form of a spring extends between the finger tabs 124 to bias the jaws 122 toward the closed position illustrated in FIG. 15. When the finger tabs 124 are squeezed together, however, the jaws 122 will separate.

With further reference to FIG. 15, extending inwardly from each finger tab 124 is a needle clamping element 130. The clamping elements 130 form an inner circular opening 132 through which a needle shaft can be passed. When the jaws 122 of the needle holder 120 are closed, and therefore the finger tabs 124 have not been moved toward each other, the needle shaft can easily slide through the opening 132. When the finger tabs 124 have been moved toward each other, however, so as to separate the jaws 122, the clamping elements 130 squeeze the needle shaft to prevent the needle from sliding along the opening 132.

FIG. 16 shows the needle holder 120 attached to the arm 116 of the needle support 110. As is shown in that figure, a needle shaft 102 has been passed through the opening 132. In the orientation of FIG. 15, the jaws 122 are securely clamped onto the arm 116 so that the needle holder 120 will not move relative to the arm, and the needle shaft 102 can easily slide along the opening 132. If the finger tabs 124 are squeezed together, however, the jaws 122 would open so that the position of the needle holder 120 relative to the arm 116 could be changed. In addition, when the finger tabs 124 are squeezed together, the clamping elements 130 pinch the needle shaft 102 so that the needle 100 cannot shift relative to the needle holder 120. With such functionality, the physician can adjust the position and angle of the needle holder 120 and the needle 100 by squeezing the finger tabs 124. When the desired position and angle have been achieved, however, the finger tabs 124 can be released, at which point the jaws 122 of the holder will clamp onto the arm 116 and the needle shaft 102 will be released so that it can be advanced into the patient.

Figure 17:
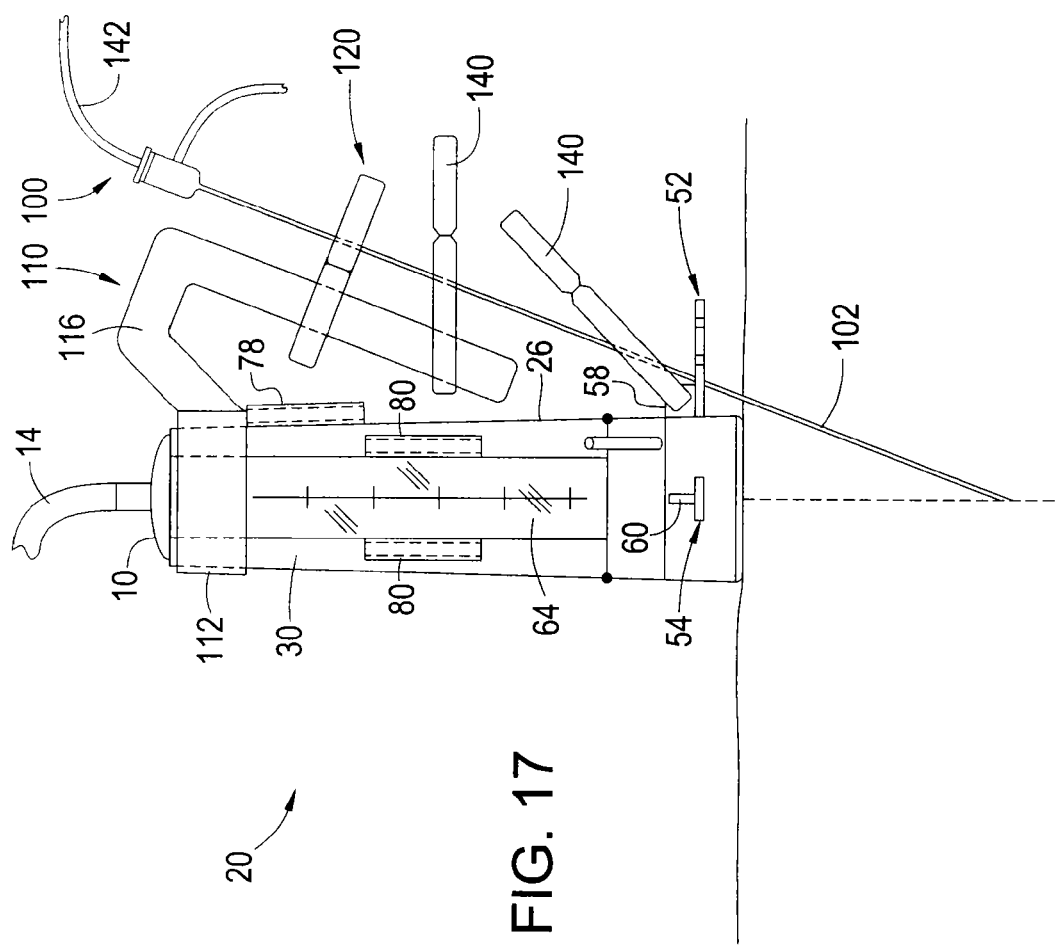
FIG. 17 is a side view of the ultrasound probe cover of FIG. 2 applied to an ultrasound probe, illustrating holding of a needle using the needle support of FIG. 13 and the needle holder of FIG. 15.
Figure 18:
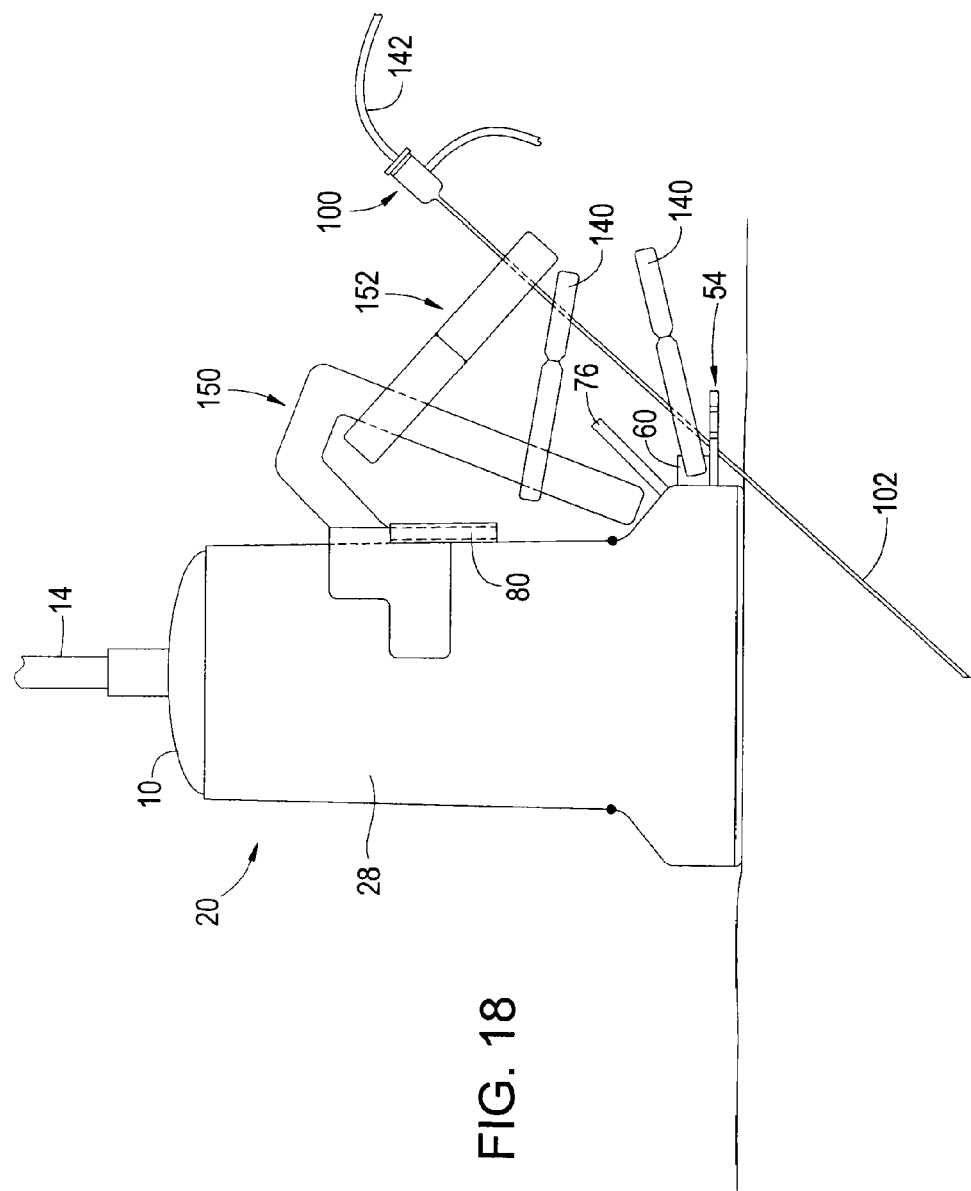
FIG. 18 is a rear view of the ultrasound probe cover of FIG. 2 applied to an ultrasound probe, illustrating holding of a needle using a further needle support and the needle holder.

FIG. 17 illustrates use of the needle support 110 and the needle holder 120 in an out-of-plane procedure. As is shown in that figure, the needle 100 is securely held in a desired orientation using the support 110 and the holder 120. As is further shown in FIG. 17, additional clips 140 can be attached to the arm 116 and the vertically-aligned tab 58 to provide additional support for the needle 100. Once the needle 100 has been advanced into the patient to the target region, a catheter 142 can be advanced through the needle. FIG. 18 illustrates use of a similar needle support 150 and the needle holder 152 in an in-plane procedure.

Although independent needle supports and needle holders have been described and illustrated, it is noted that the needle supports and/or holders can alternatively be integrated into the design of the cover 20. In such a case, no assembly would be required.

The invention claimed is:

1. Apparatus for facilitating ultrasound-assisted needle placement for drug delivery, the apparatus comprising:
   an ultrasound probe cover adapted to receive an ultrasound probe, the cover unitarily formed from polymeric material and comprising:
   a front wall, a rear wall, and a first lateral wall;
   a first needle guide comprising a first elongated member extending from the front wall, and a second needle guide comprising a second elongated member extending from the first lateral wall, each elongated member of each needle guide comprising multiple needle slots in the elongated member, the slots positioned at different distances from the respective wall, each needle slot adapted to receive the shaft of a needle and guide the needle into a patient adjacent the cover, wherein the first needle guide is adapted to guide the needle during an out-of-plane approach and the second needle guide is adapted to guide the needle during an in-plane approach;

a first mirror on the front wall adjacent the first needle guide, the first mirror marked with a first vertical line adapted to assist a physician in aligning the needle relative to the probe when using the out-of-plane approach, the first mirror further marked with first depth markers along the length of the first vertical line that form a first scale that provides an indication of a depth of insertion of the needle; and a second mirror on the first lateral wall adjacent the second needle guide, the second mirror marked with a second vertical line adapted to assist a physician in aligning the needle relative to the probe when using the in-plane approach, the second mirror further marked with second depth markers along the length of the second vertical line that form a second scale that provides an indication of a depth of insertion of the needle.

2. The apparatus of claim 1, wherein the elongated member of each of the first and second needle guides extends in a direction that is generally perpendicular to the respective wall from which it extends.

3. The apparatus of claim 2, wherein the needle slots of each of the first and second elongated members of each of the first and second needle guides extend inward from a lateral edge of the respective elongated member along a diagonal direction toward the respective wall from which the elongated member extends.

4. The apparatus of claim 1, wherein the cover further comprises a base plate adapted to contact the patient, the base plate comprising an ultrasound window and an absorbent member adapted to hold sterilizing fluid.

5. The apparatus of claim 4, wherein the base plate further includes a peripheral skirt adapted to retain the sterilizing fluid in place between the cover and the patient.

6. The apparatus of claim 1, further comprising at least two markers positioned on the cover at discrete positions and adapted to be used in conjunction with the first and second mirrors to assist a physician in aligning the needle with the cover.

7. The apparatus of claim 1, wherein the cover further comprises a reference element in the form of a third elongated member that extends from the first lateral wall of the cover and wherein the third elongated member forms a 45° angle with a base of the cover, thereby providing an indication of a 45° approach angle when inserting the needle using the in-plane approach.

8. The apparatus of claim 1, further comprising a needle support that extends out from the first wall, the needle support being adapted to support the needle in a desired orientation relative to the cover.

9. The apparatus of claim 8, wherein the cover comprises mounting elements with which the needle support mounts to the cover.

10. The apparatus of claim 8, further comprising a needle holder associated with the needle support, the needle holder being adapted to securely hold the needle.

11. The apparatus of claim 10, wherein the needle holder comprises clamping jaws adapted to grip the needle support and an inner circular opening in the needle holder through which a needle shaft can be passed.

12. A method for facilitating ultrasound-assisted needle placement for drug delivery, the method comprising:
attaching a sterile cover to an ultrasound probe, the sterile cover unitarily formed from polymeric material and comprising:
a front wall, a rear wall, and a first lateral wall;
a first needle guide comprising a first elongated member extending from the front wall and a second needle guide comprising a second elongated member extending from the first lateral wall, each elongated member of each needle guide comprising-multiple needle slots in the elongated member, the slots positioned at different distances from the respective wall, each needle slot adapted to receive the shaft of a needle and guide the needle into a patient adjacent the cover, wherein the first needle guide is adapted to guide the needle during an out-of-plane approach and the second needle guide is adapted to guide the needle during an in-plane approach;
a first mirror on the front wall adjacent the first needle guide, the first mirror marked with a first vertical line adapted to assist a physician in aligning the needle relative to the probe when using the out-of-plane approach; and
a second mirror on the first lateral wall adjacent the second needle guide, the second mirror marked with a second vertical line adapted to assist a physician in aligning the needle relative to the probe when using the in-plane approach;
placing a needle in one of the first or second needle guides of the cover; and
advancing the needle into a patient with the assistance of the first or second needle guide.

13. The method of claim 12, further comprising securing the needle in a desired position relative to the cover using needle support means and holding means associated with the cover.

14. The method of claim 13, further comprising advancing a catheter or a guidewire through the needle while the needle is secured by the support means and holding means.

\* \* \* \* \*